United States Patent
Leff et al.

(10) Patent No.: US 12,121,268 B2
(45) Date of Patent: Oct. 22, 2024

(54) MODULAR ORTHOPEDIC IMPLANTS, INSTRUMENTS, AND NAVIGATION METHODS

(71) Applicant: GLOBUS MEDICAL, INC., Audubon, PA (US)

(72) Inventors: David Leff, Philadelphia, PA (US); Jeff Nichols, Medford, NJ (US); Matthew Bechtel, Philadelphia, PA (US); Darren Clutter, Barto, PA (US); Richard Pidgeon, Phoenixville, PA (US); Neil Crawford, Chandler, AZ (US); Thomas Calloway, Pelham, NH (US)

(73) Assignee: Globus Medical, Inc., Audubon, PA (US)

( * ) Notice: Subject to any disclaimer, the term of this patent is extended or adjusted under 35 U.S.C. 154(b) by 187 days.

(21) Appl. No.: 17/369,327

(22) Filed: Jul. 7, 2021

(65) Prior Publication Data

US 2023/0010173 A1    Jan. 12, 2023

(51) Int. Cl.
| | |
|---|---|
| *A61B 17/70* | (2006.01) |
| *A61B 17/88* | (2006.01) |
| *A61B 34/20* | (2016.01) |
| *A61B 34/30* | (2016.01) |
| *A61B 90/00* | (2016.01) |

(52) U.S. Cl.
CPC ........ *A61B 17/704* (2013.01); *A61B 17/7032* (2013.01); *A61B 17/7076* (2013.01); *A61B 17/7082* (2013.01); *A61B 17/8888* (2013.01); *A61B 34/20* (2016.02); *A61B 34/30* (2016.02); *A61B 90/39* (2016.02); *A61B 2034/2065* (2016.02); *A61B 2034/2068* (2016.02); *A61B 2090/3937* (2016.02)

(58) Field of Classification Search
CPC .............. A61B 17/888; A61B 17/8888; A61B 17/8615; A61B 17/7082; A61B 17/7076; B25B 23/105; B25B 23/106; B25B 23/108

See application file for complete search history.

(56) References Cited

U.S. PATENT DOCUMENTS

| | | |
|---|---|---|
| 3,825,048 A | 7/1974 | Triska |
| 5,139,499 A | 8/1992 | Small et al. |
| 5,466,237 A | 11/1995 | Byrd, III et al. |

(Continued)

FOREIGN PATENT DOCUMENTS

| | | |
|---|---|---|
| DE | 20014911 U1 | 11/2000 |
| JP | 5877042 B2 | 3/2016 |

(Continued)

*Primary Examiner* — Julianna N Harvey
*Assistant Examiner* — Anna V. Little

(57) ABSTRACT

Modular orthopedic implants, associated instruments, and navigation methods. The modular orthopedic fixation assembly may include a modular bone fastener and a modular tulip head configured to be installed separately. The modular bone fastener may be installed and tracked with a screw extender instrument having an outer sleeve and an inner shaft coupled to the bone fastener. The screw extender instrument may continue to track the location and orientation of the bone throughout the surgical procedure for navigational integrity. The modular tulip head may be assembled to the bone fastener with a head inserter instrument, which ensures the modular head is properly seated on the installed bone fastener.

8 Claims, 14 Drawing Sheets

(56) References Cited

U.S. PATENT DOCUMENTS

| | | | |
|---|---|---|---|
| 5,797,911 A | 8/1998 | Sherman et al. | |
| 7,137,322 B2 | 11/2006 | Mark et al. | |
| 7,174,615 B2 | 2/2007 | Mark et al. | |
| 7,226,456 B2 | 6/2007 | O'Neil et al. | |
| 7,335,202 B2 | 2/2008 | Matthis et al. | |
| 7,846,190 B2 | 12/2010 | Ball | |
| 7,909,834 B2 | 3/2011 | Selover | |
| 1,929,975 A1 | 10/2011 | Mosimann | |
| 8,277,490 B2 | 10/2012 | Freeman et al. | |
| 8,377,102 B2 | 2/2013 | Jackson | |
| 8,491,641 B2 | 7/2013 | Nihalani | |
| 8,663,290 B2 | 3/2014 | Doubler et al. | |
| 8,777,960 B2 | 7/2014 | Murray et al. | |
| 9,078,705 B2 | 7/2015 | Matthis et al. | |
| 9,451,999 B2 | 9/2016 | Simpson et al. | |
| 9,452,007 B1 | 9/2016 | McGuire et al. | |
| 9,615,858 B2 | 4/2017 | Doubler et al. | |
| 9,655,656 B2 | 5/2017 | Whipple | |
| RE46,422 E | 6/2017 | Foley et al. | |
| 9,956,020 B2 | 5/2018 | Benson et al. | |
| 10,022,157 B2 | 7/2018 | Walker et al. | |
| 10,034,691 B1 | 7/2018 | Lish | |
| 10,194,951 B2 | 2/2019 | Jackson et al. | |
| 10,335,204 B2 | 7/2019 | Matthis et al. | |
| 10,335,247 B2 | 7/2019 | Lechner et al. | |
| 10,426,535 B2 | 10/2019 | Zander et al. | |
| 10,492,834 B2 | 12/2019 | May et al. | |
| 10,603,082 B2 | 3/2020 | Lish | |
| 10,702,343 B2 | 7/2020 | Kozak et al. | |
| 10,779,893 B2 | 9/2020 | Elliott et al. | |
| 10,792,108 B2 | 10/2020 | Yang et al. | |
| 10,799,300 B2 | 10/2020 | Elliot et al. | |
| 10,828,112 B2 | 11/2020 | Syverson et al. | |
| 10,864,057 B2 | 12/2020 | Chappuis et al. | |
| 10,945,806 B2 | 3/2021 | Wall et al. | |
| 2004/0133207 A1* | 7/2004 | Abdou | A61B 17/7059 606/279 |
| 2006/0104707 A1* | 5/2006 | Neubauer | A61B 90/39 401/199 |
| 2007/0068349 A1* | 3/2007 | Min | B25B 15/008 81/436 |
| 2009/0287218 A1 | 11/2009 | Beger et al. | |
| 2011/0040338 A1 | 2/2011 | Jackson | |
| 2012/0041490 A1 | 2/2012 | Jacob et al. | |
| 2012/0215232 A1* | 8/2012 | Olsen | A61B 17/8888 606/139 |
| 2013/0060146 A1* | 3/2013 | Yang | G01B 11/25 600/476 |
| 2016/0220277 A1* | 8/2016 | Rezach | A61B 17/7038 |
| 2016/0262819 A1* | 9/2016 | May | A61B 17/8888 |
| 2018/0014862 A1* | 1/2018 | Raina | A61B 17/708 |
| 2018/0185076 A1* | 7/2018 | Zander | A61B 17/862 |
| 2018/0280067 A1 | 10/2018 | Bjork et al. | |
| 2019/0150989 A1* | 5/2019 | Biester | A61B 17/7082 |
| 2019/0254730 A1* | 8/2019 | Rohlfing | A61B 17/8888 |
| 2019/0269469 A1 | 9/2019 | Bush et al. | |
| 2020/0008884 A1 | 1/2020 | LaVallee et al. | |
| 2020/0268452 A1 | 8/2020 | Rezach et al. | |
| 2020/0330137 A1 | 10/2020 | Rezach | |
| 2020/0360091 A1 | 11/2020 | Murray et al. | |
| 2020/0360106 A1* | 11/2020 | Ghanam | A61B 90/11 |
| 2020/0390478 A1 | 12/2020 | Rodriguez et al. | |
| 2021/0045791 A1* | 2/2021 | Perrow | B25B 15/02 |
| 2021/0068881 A1 | 3/2021 | Wall | |

FOREIGN PATENT DOCUMENTS

| | | |
|---|---|---|
| KR | 20120056215 A | 6/2012 |
| WO | 2012128825 A1 | 9/2012 |

* cited by examiner

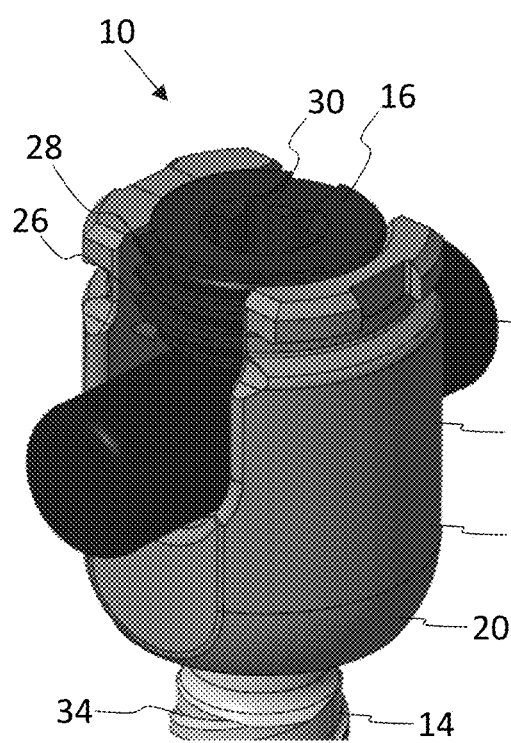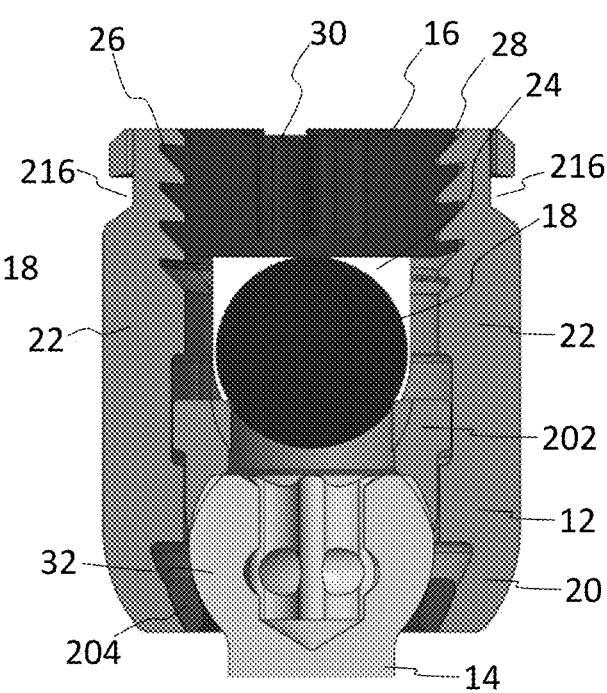
FIG. 1
FIG. 2

MODULAR ORTHOPEDIC IMPLANTS, INSTRUMENTS, AND NAVIGATION METHODS

FIELD OF THE INVENTION

The present application relates generally to orthopedic fixation devices, such as pedicle implants, associated instruments, and navigation methods, for example, for spine surgery.

BACKGROUND OF THE INVENTION

Many types of spinal irregularities cause pain, limit range of motion, or injure the nervous system within the spinal column. These irregularities may result from, without limitations, trauma, tumor, disc degeneration, and disease. Often, these irregularities are treated by immobilizing a portion of the spine. This treatment typically involves affixing a bone screw to one or more vertebrae and connecting the bone screws to an elongate spinal rod that stabilizes members of the spine.

The screw may be a pedicle screw having a tulip head for coupling the screw to the elongate spinal rod. There exists a need for improved designs of the screws, instruments for implantation, and enhanced methods for placement and assembly of the devices.

SUMMARY OF THE INVENTION

To meet this and other needs, orthopedic implants, assemblies, systems, instruments, and methods are provided. The bone fastener may include a modular screw and tulip head for securing the spinal rod therein. The modular screw may be deployed first and the modular head may be later deployed and assembled onto the screw during the surgical procedure. The bone fastener may be implanted, for example, in open, semi-open, or percutaneous approaches to the posterior spine with or without the assistance of navigation and/or a robotic system. The navigation methods may allow for assisted placement of the modular screws, tracking of the vertebral bodies, and/or assembly of the modular heads onto the modular screws during the surgical procedure.

According to one embodiment, a modular orthopedic fixation assembly includes a modular screw, a modular tulip head assembly, and a threaded locking cap. The modular screw includes a screw head defining a drive and engagement recess and a shaft configured for engaging bone. The modular tulip head assembly includes a tulip head having two arms defining a rod slot therebetween, and a saddle and a clip configured to secure the screw head of the bone fastener in the tulip head. The threaded locking cap is threadable between the two arms of the tulip head to secure a rod therein. The modular screw and tulip head assembly may be installed separately and assembled together during the surgical procedure.

According to another embodiment, a system for installing a modular orthopedic fixation assembly includes the modular screw and tulip head assembly and a screw extender instrument. The screw extender instrument is configured to engage with the screw head. The screw extender instrument includes an outer sleeve and an inner shaft extending through the outer sleeve receivable in the drive and engagement recess of the screw head. Movement of the outer sleeve and/or inner shaft secures the screw extender instrument to the screw head.

The screw extender instrument may be secured to the screw head by one of several different mechanisms. In one embodiment, the screw extender instrument includes one or more ball bearings receivable in the drive and engagement recess of the screw head, thereby allowing for a rigid connection between the screw extender instrument and the screw head. The drive and engagement recess in the screw head may include a recessed drive portion configured to interface with the outer sleeve and one or more recessed engagement portions configured to interface with the one or more ball bearings of the screw extender instrument. The engagement portions may each define an undercut with a circular cross-section sized and dimensioned to interface with the ball bearing of complimentary size and shape. The screw extender instrument may include a helical ramp at a distal end of the inner shaft and when the inner shaft is rotated and/or translated, the ball bearing is seated into the engagement portion of the screw head. The screw extender instrument may include a pair of ball bearings and the inner shaft may include a pointed tip that when translated downwardly forces the ball bearings outwardly into the engagement portions of the screw head. In another embodiment, the screw extender instrument includes a threaded portion along an outer portion of the outer sleeve, which secures the instrument to the screw head. In another embodiment, the screw extender instrument includes a prong extending from the outer sleeve configured to wedge between the screw head and the inner shaft. In yet another embodiment, the screw extender instrument includes one or more flexible portions separated by one or more slits, and the flexible portions can be expanded when the inner shaft is translated toward the screw head, thereby securing the instrument to the screw head.

Any of the screw extender instruments may be retained by a two-part screw driver instrument. The screw extender instrument may couple to the screw driver instrument to allow a user to align the screw with an intended trajectory and apply torque to the screw. The proximal end of the outer sleeve of the screw extender instrument may include a drive interface and a circumferential groove which allows the screw extender instrument to be rigidly constrained to the screwdriver instrument. A female drive seat may mate with the drive interface of the outer sleeve and a flexible mechanical spring may engage with the groove in the back portion of the screw extender. The proximal end of the inner shaft of the screw extender may include a ribbed neck which is received in a handle portion of the screw driver, thereby allowing for rotation and/or translation of the inner shaft of the screw extender instrument.

In some embodiments, the screw extender instruments or other instruments may include one or more tracking elements configured to be tracked by a navigation and/or robotic system. In one embodiment, the instrument includes a tracking array axially constrained or attached thereto, which is used to locate the axis and location of the tip of the screw for navigated placement. The instrument may have an outer body portion with an outer diameter sized and configured to mate with a guide tube of a robotic system. In another embodiment, the instrument includes one or more machine vision targets for instrument recognition and tracking by a navigation and/or robotic system. The machine vision targets may include longitudinal, circumferential, or other suitable targets that are marked, coated, or cut directly on the instrument body. In addition, one or more areas of the instrument may include non-reflective coatings or surface treatments to reduce reflections or glare from bright operative lights. In yet another embodiment, the tracking element includes a two marker array with fiducial markers aligned along a central axis of the screw for navigated and/or robotic screw placement.

According to another embodiment, a method of installing a modular orthopedic fixation device in bone includes one or more of the following steps: (1) attaching a screw extender instrument to a modular screw having a screw head and a shaft, wherein the screw extender instrument includes an outer sleeve and an inner shaft extending through the outer sleeve receivable in a recess in the screw head, wherein movement of the outer sleeve and/or inner shaft secures the screw extender instrument to the screw head; (2) inserting the modular screw into bone with the screw extender instrument; and (3) connecting a tulip head assembly to the screw head, wherein the tulip head assembly includes a tulip head having two arms defining a rod slot therebetween, a saddle received in a first groove and a clip received in a second groove, wherein when the screw head contacts a bottom of the clip, the clip moves upward to an upper portion of the second groove, and expands the clip until the screw head passes through the clip, thereby assembling the tulip head to the screw. The method may also include: (4) positioning a rod between the two arms and into the rod slot of the tulip head; and (5) threading a locking cap downwardly between the two arms of the tulip head, wherein the rod presses against the saddle, and the saddle presses against the screw head, thereby securing the rod and the modular screw.

According to yet another embodiment, a system of tracking bone with a modular orthopedic fixation assembly may include first and second modular screws each including a screw head defining a recess and a shaft configured for engaging bone. First and second navigatable screw extender instruments may be configured to engage with the screw heads of the first and second modular screws, respectively. Each screw extender instrument may include an outer sleeve and an inner shaft extending through the outer sleeve receivable in the recess of the screw head. Movement of the outer sleeve or inner shaft secures the screw extender instrument to the screw head. Each navigatable screw extender instrument may include a two marker array with fiducial markers aligned along a central axis of the screw for navigated and/or robotic screw placement. Once the first and second modular screws have been placed, the first and second screw extender instruments continue to track the location and orientation of the bone using the location and orientation of the placed screws.

The system may further include one or more of the following elements. One or both of the first and second screw extender instruments may act as a local dynamic reference base, thereby improving navigation integrity. The orientation of the central axes of the screws and first and second screw extenders may be recorded at an initial position, vectors defining the central axes of the screw extenders may be calculated, and if the vectors change, navigation integrity has been lost. The vectors may be compared to the original orientation of the central axes of the screws to define a transformation matrix that corresponds to translation and/or rotation of the bone. The transformation matrix may be applied to a vertebral body coordinate system to update any movement in space. The orientation and position of the central axes of the screws may be recorded at an initial position. Locations of the fiducial markers may be modeled by calculating their distance along the central axes of the screw extenders defining an array to be tracked and recognized. If the array is not recognized, navigation integrity has been lost.

According to yet another embodiment, a head inserter instrument may be provided to attach the tulip head to the screw head. The tulip head assembly may be engaged with the head inserter instrument having an external sleeve with inwardly facing prongs configured to engage with a groove on an outside of the tulip head. The head inserter instrument may include a sensing pin extending beyond the external sleeve. When the sensing pin is depressed by the screw head and the tulip head is fully seated on the screw head, the external sleeve is released from the tulip head.

Also provided are kits including implants of varying types and sizes, rods, various instruments and tools, and other components for performing the procedure.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein:

FIG. 1 shows a perspective view of a modular bone fastener assembly including a modular screw and a tulip head according to one embodiment;

FIG. 2 shows a cross-sectional view of the modular bone fastener assembly of FIG. 1 retaining a spinal rod;

DETAILED DESCRIPTION OF THE INVENTION

Figure 3:
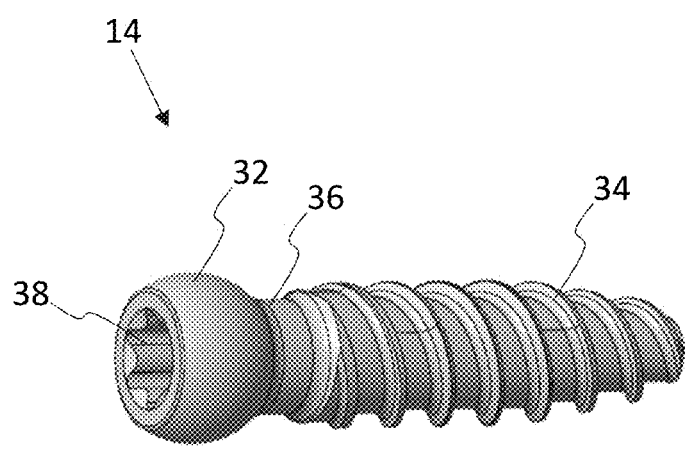
FIG. 3 is a perspective view of the modular screw from the modular bone fastener assembly of FIG. 1.

Embodiments of the disclosure are generally directed to orthopedic implants, assemblies, systems, instruments, and methods. Specifically, embodiments are directed to modular bone fastener assemblies configured to secure one or more spinal rods, installation instruments, and navigation methods. The modular bone fastener may include a modular screw configured to be inserted into bone with or without navigation and/or robotic assistance. One or more screw extender instruments may provide for secure attachment to and improved maneuverability of the modular screw. After screw installation, a modular head may be deployed and attached to the modular screw with or without navigation and/or robotic assistance. Navigational tracking of the procedure and/or a robotic system may be provided, for example, for accurate placement of the modular screw and/or tulip head, tracking of the vertebral bodies, assembly of the modular head onto the modular screw, and/or intraoperative feedback. These implants and instruments may be used in open and percutaneous approaches to the posterior spine with or without assistance of a navigation or robotic system. Although generally described with reference to the spine, it will be appreciated that the devices and systems described herein may be applied to other orthopedic locations in the body and other medical applications, such as trauma.

Additional aspects, advantages and/or other features of example embodiments of the invention will become apparent in view of the following detailed description. It should be apparent to those skilled in the art that the described embodiments provided herein are merely exemplary and illustrative and not limiting. Numerous embodiments or modifications thereof are contemplated as falling within the scope of this disclosure and equivalents thereto.

Referring now to FIGS. 1-2, an orthopedic fixation device, implant, or bone fastener assembly 10 is shown according to one embodiment. The implant or bone fastener assembly 10 may include a tulip head or modular head 12, a bone fastener or modular screw 14, and a locking cap 16 for securing a spinal rod 18 in the modular head 12. In the case of a polyaxial assembly 10, tightening the locking cap 16 compresses the rod 18 into the tulip head 12, thereby restricting motion of the modular screw 14 and forming a rigid construct. The modular screw 14 may be deployed independently from the modular head 12. For example, the modular screw 14 may be first installed in bone and the modular head 12 may be later deployed and assembled onto the modular screw 14 during the surgical procedure. Alternatively, the modular head 12 and screw 14 may be pre-assembled prior to installation.

The tulip head 12 may include a body 20 and arms 22 that extend upwardly from the body 20. A central bore 24 may extend through the tulip head 12. The opposed arms 22 may define a U-shaped channel, transverse to the bore 24, sized and configured to accept the rod 18. Each of the arms 22 has an interior surface defining a threaded portion 26 for engaging the threaded locking cap 16. The outer surface of the tulip head 12 may define one or more tool engagement grooves 216 for holding and maneuvering the tulip head 12 with a suitable tool.

The rod 18 may be secured in the tulip head 12 with the locking cap 16. The locking cap 16 may define an outer threaded portion 28 configured to interface with the inner threaded portion 26 of the tulip head 12. The locking cap 16 may be in the form of a set screw with a drive recess 30 configured to be engaged by a driving instrument, which is able to insert and tighten the locking cap 16 in the tulip head 12. The bottom of the locking cap 16 may be flat or otherwise configured to ensure consistent contact with the rod 18.

Turning now to FIG. 3, the bone fastener 14 may include a bone screw, anchor, clamp, or the like configured to engage bone. In the embodiment shown, the bone fastener 14 is a modular bone screw 14, such as a pedicle screw. The modular screw 14 extends from a proximal end with a screw head 32 to a distal end configured to engage bone. The modular screw 14 has a threaded shaft 34 connected to the screw head 32 by a neck portion 36. It will be appreciated that the threaded shaft 34 may have a number of different features, such as lead(s), thread pitch, thread angle, shaft diameter to thread diameter, overall shaft shape, and the like, depending, for example, on the particular application. The threaded shaft 32 may terminate at a tip at the distal end, which may be blunt, pointed, or otherwise configured to engage bone. While the screw head 32 may have any general shape, in the case of a polyaxial fastener, at least a portion of the screw head 32 may have a curved surface in order to allow for rotational movement and/or angular adjustment of the bone fastener 14 with respect to the tulip head 12. For example, at least a portion of the screw head 32 may be shaped to form a portion of a ball or a sphere. The spherical screw head 32 may define one or more drive and/or engagement surfaces 38, for example, that can be engaged by a screw-driving instrument or other device. In one embodiment, the bone screw head 32 defines a hexalobular drive recess 38 for driving the screw 14 into bone. It will be appreciated that any suitably shaped tool engagement drive surface 38 may be provided.

Turning now to FIGS. 4-7, alternative embodiments of drive and engagement features 38 that mate with corresponding screw extender instruments 40, 60, 70, 80 are shown. The drive and engagement recess 38 is configured to create a rigid connection between the modular screw 14 and the screw extender instrument 40, 60, 70, 80. The screw extender instrument 40, 60, 70, 80 may be attached to the modular screw 14 before, during, or after insertion of the screw 14 into the vertebral body. The screw extender instruments 40, 60, 70, 80 allow for a rigid and slim screwdriver design that may minimize tissue disruption during retraction, maximize visualization and access by not obstructing working pathways for other tools, guide insertion of the modular head into engagement with the screw, and allow for tracking of vertebral bodies. The alternative interface designs described herein may allow for improved manufacturability, enhanced ease of use, and varying amounts of rigidity between the instrument and the screw 14.

Figure 4A:
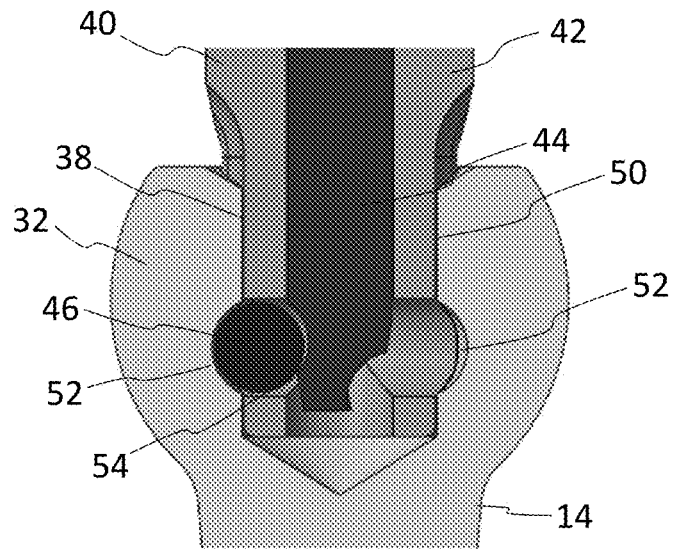
FIGS. 4A-4B show cross-sectional views of examples of internal drive and engagement interfaces mated with respective screw extender instruments.
Figure 4B:
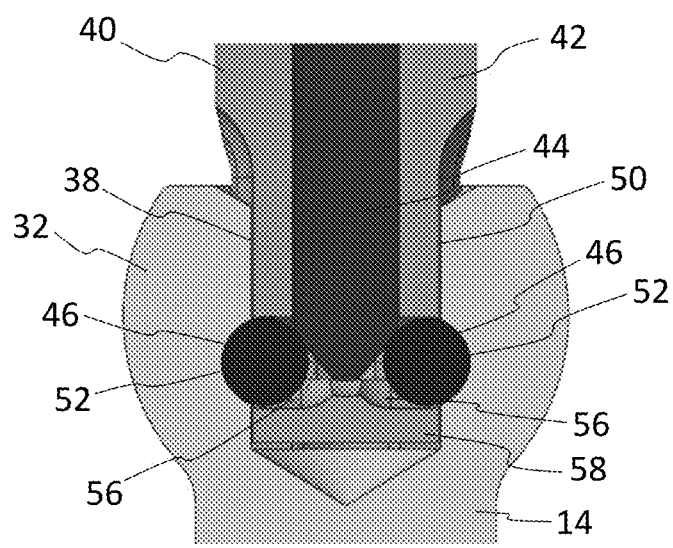

FIGS. 4A-4B show cross-sectional views of two alternative screw extender instruments 40 engaged with the screw head 32 with one or more ball bearings 46. The screw extender instruments 40 each include an outer sleeve or outer shaft 42, an inner shaft 44 extending through the outer shaft 42, and one or more ball bearings 46. The inner drive and engagement recess 38 in the screw head 32 includes a recessed drive portion 50 configured to interface with the outer shaft 42 and one or more recessed engagement portions 52 configured to interface with the one or more ball bearings 46 of the screw extender instrument 40. The drive portion 50 may interface with the outer shaft 42, for example, with a Torx drive or other suitable screw drive mechanism. Within the drive portion 50, each recessed engagement portion 52 may define an undercut with a circular cross-section sized and dimensioned to interface with the ball bearing 46 of complimentary size and shape. When the one or more ball bearings 46 are received in the one or more engagement portions 52, disengagement of the screw extender instrument 40 is thereby prevented allowing for a rigid connection between the instrument 40 and the screw head 32. One ball bearing 46 may be engaged to allow for a simple mechanism (shown in FIG. 4A) or multiple ball bearings 46 may be engaged to allow for a more robust mechanism (shown in FIG. 4B).

In the embodiment shown in FIG. 4A, the screw extender instrument 40 includes a single ball bearing 46 configured to engage with one of the engagement portions 52 of the screw head 32. The drive portion 50 of the screw head 32 is engaged by the similarly-shaped tip of the screw extender instrument 42. The modular screw drive portion 50 defines a plurality of engagement portions 52 with undercuts or grooves having generally circular or spherical portions that interface with the ball bearing 46. The ball bearing 46 may be translated into engagement with one of the engagement portions 52 by movement of the inner shaft 44 of the screw extender instrument 40. For example, a helical screw cut or ramp 54 at the distal end of the inner shaft 44 may facilitate translation of the ball 46 by rotation and/or translation of the inner shaft 44. After the inner shaft 44 is rotated and/or translated downwardly, the ball bearing 46 is seated in one of the engagement portions 52. Once engaged with the engagement portion 52, the ball bearing 46 is configured to prevent disengagement of the screw extender instrument 40 from the screw 14, thereby forming a temporary rigid connection.

In the embodiment shown in FIG. 4B, the screw extender instrument 40 includes a pair of ball bearings 46 configured to engage with two engagement portions 52 in the screw head 32. When the inner shaft 44 is rotated and/or translated, the pointed tip of the inner shaft 44 forces the ball bearings 46 outwardly and into the engagement recesses 52. The ball bearings 46 may be caged within the assembly at the outermost and innermost extensions of their travel by ramped spherical cuts 56. A caging component or base 58 may be added to the bottom to facilitate assembly and manufacturability of the caging cuts 56. The caging base 58 may be welded, slotted, or pinned to the screw extender instrument 42. Alternatively, the balls 46 may be retained in the assembly, for example, by tack welding, permanently deforming the drive feature, or other suitable means. Over-translation of the ball bearings 46 into the grooves 52 compresses the screw extender instrument 40 into the drive feature. After the inner shaft 44 is rotated and/or translated downwardly, the ball bearings 46 are seated in respective engagement portions 52. Once engaged with the engagement portions 52, the ball bearings 46 are configured to prevent disengagement of the screw extender instrument 40 from the screw 14, thereby forming a temporary rigid connection.

Figure 5:
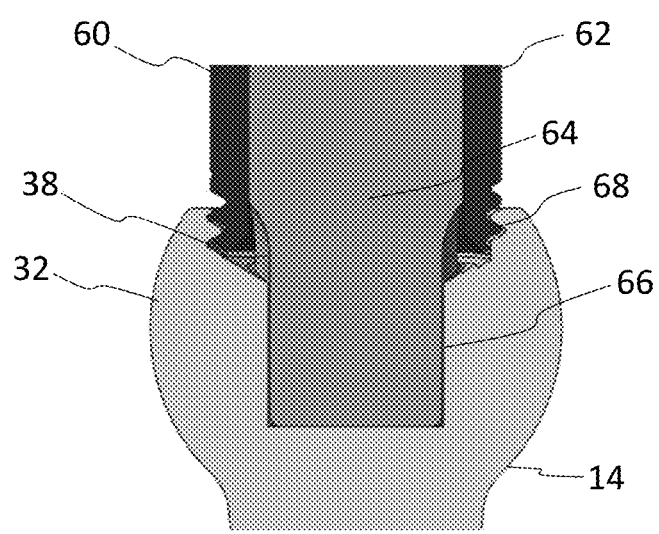
FIG. 5 is a cross-sectional view of a threaded interface between a screw extender instrument and the screw head according to one embodiment.

Turning now to FIG. 5, a cross-sectional view of a screw extender instrument 60 engaged with the screw head 32 via an external threaded sleeve 62 is shown according to one embodiment. The screw extender instrument 60 includes an outer sleeve 62 and inner shaft 64 extending therethrough. In this embodiment, the inner drive and engagement recess 38 in the screw head 32 includes a central recessed drive portion 66 configured to interface with the inner shaft 64 and a threaded engagement portion 68 configured to interface with the threaded outer sleeve 62 of the instrument 60. The internal threads 68 in the screw head 32 mate with the threaded outer sleeve 62 which is axially constrained to the inner shaft 64. Tightening of these threads 68 pulls the drive feature 66 into engagement to create a rigid connection between the screw head 32 and the instrument 60.

Figure 6A:
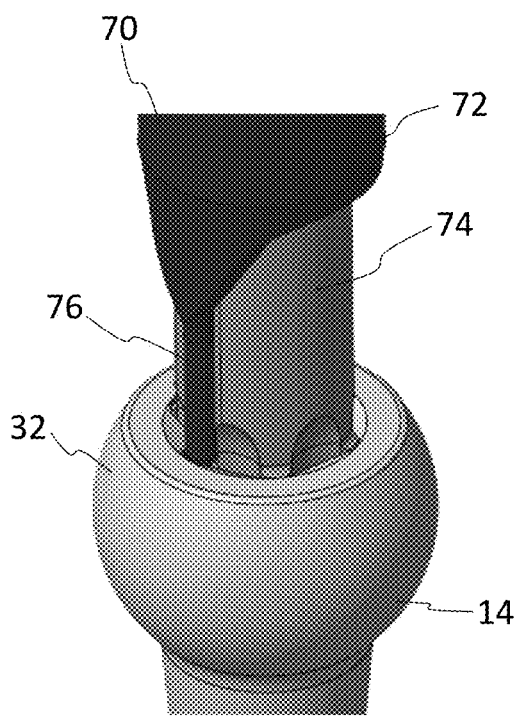
FIGS. 6A-6B show perspective and cross-sectional views, respectively, of a screw extender instrument with a translatable prong configured to temporarily secure the instrument to the screw head according to one embodiment.
Figure 6B:
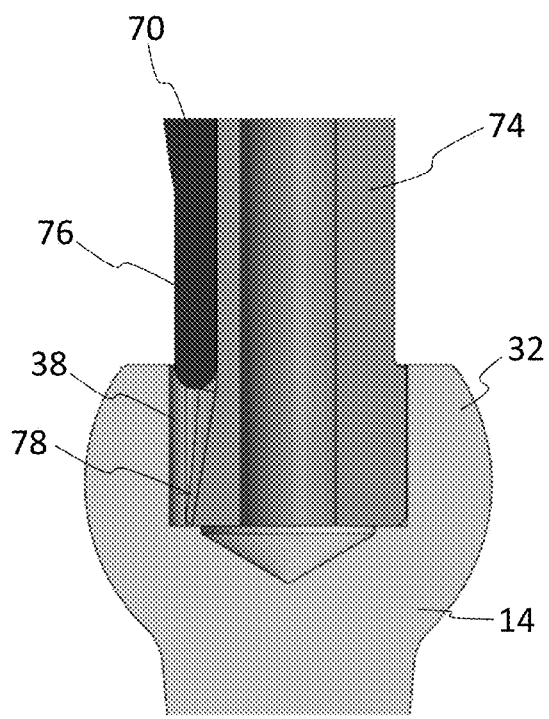

Turning now to FIGS. 6A-6B, a perspective view and a cross-sectional view, respectively, of a screw extender instrument 70 engaged with a screw head 32 via one or more wedging prongs 76 is shown according to one embodiment. The screw extender instrument 70 includes an outer sleeve 72 and inner shaft 74 extending therethrough. In this embodiment, the inner drive recess 38 in the screw head 32 includes a central recessed drive portion configured to interface with the inner shaft 74 and the outer sleeve 72 includes one or more prongs 76 configured to secure the instrument 70 to the screw head 32. The drive portion 38 may interface with the inner shaft 74, for example, with a Torx drive or other suitable screw drive mechanism. The inner drive recess 38 and/or the inner shaft 74 may define one or more ramped cuts 78 configured to receive the prong 76. The ramped cut(s) 78 are configured to displace the prong(s) 76 into the drive feature 38. For example, when the prong 76 is translated downward and is wedged between the drive portion 38 and the inner shaft 74, a rigid connection is created between the instrument 70 and the screw 14.

Figure 7A:
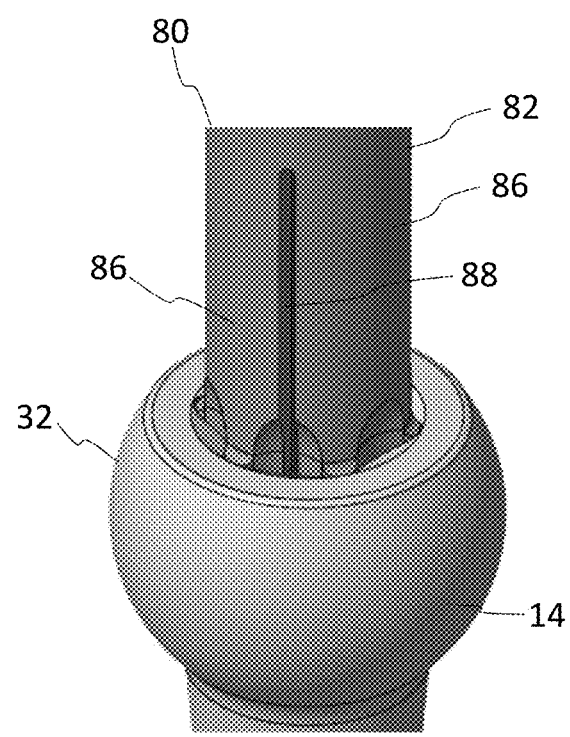
FIGS. 7A-7B show perspective and cross-sectional views, respectively, of a screw extender instrument with an expandable split drive feature according to one embodiment.
Figure 7B:
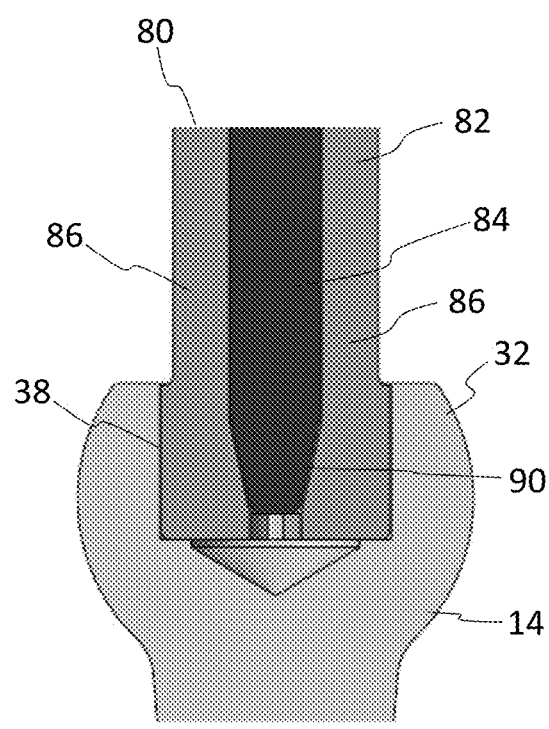

Turning now to FIGS. 7A-7B, a perspective view and a cross-sectional view, respectively, of a screw extender instrument 80 rigidly engaged with a screw head 32 via a split drive is shown according to one embodiment. The screw extender instrument 80 includes an outer sleeve 82 and inner shaft 84 extending therethrough. In this embodiment, the outer sleeve 82 of the screw extender 80 is split into one or more flexible portions 86 which can be expanded into the drive feature 38 of the screw 14. The flexible portions 86 may be separated by one or more slits 88 extending from the distal end of the outer sleeve 82 upwards a distance towards the proximal end of the sleeve 82. The outer surface of the distal end of the outer sleeve 82 may have a configuration, such as a Torx driver, configured to mate with the corresponding recess 38 in the screw head 32. When the inner shaft 84 is translated downward toward the screw 14, a ramped or tapered distal tip 90 of the inner shaft 84 presses against one or more corresponding ramped surfaces inside the outer sleeve 82, thereby expanding the distal end of the outer sleeve 82 into engagement with the screw head 32. Once expanded, the outer sleeve 82 forms a temporary rigid connection between the instrument 80 and the screw 14. When the inner shaft 84 is withdrawn away from the screw head 32, the outer sleeve 82 is permitted to disengage from the screw head 32.

Figure 8:
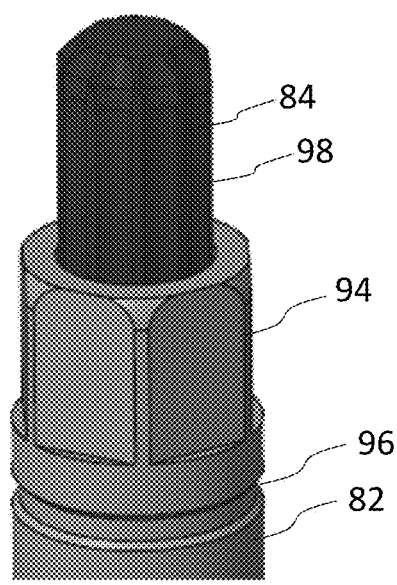
FIG. 8 is a perspective view of a proximal end of a screw extender instrument according to one embodiment.
Figure 9:
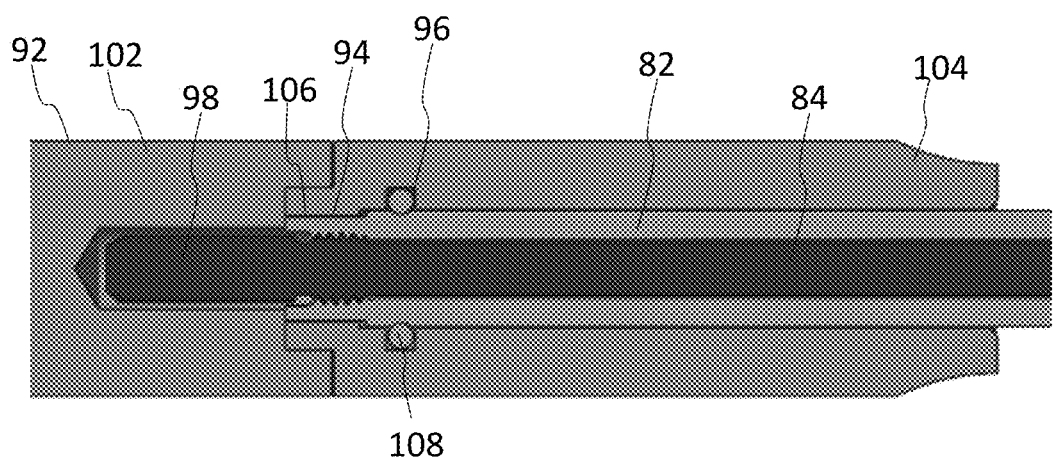
FIG. 9 shows a cross-sectional view of the proximal end of the screw extender instrument of FIG. 8 secured to a two-part screwdriver according to one embodiment.

Turning now to FIGS. 8-9, the screw extender instrument 40, 60, 70, 80 may couple to a screwdriver instrument 92 which allows the user to align the screw 14 with the intended trajectory and apply the necessary torque to insert the screw 14 into the vertebral body. FIGS. 8 and 9 are described with respect to screw extender instrument 80, but it will be appreciated that the connection interface applies equally to all of the screw extender instruments 40, 60, 70. As shown in FIG. 8, the back portion or proximal end of the screw extender instrument 80 is configured to connect to the screwdriver instrument 92. The proximal end of the outer sleeve 82 includes a drive interface 94 and a circumferential groove 96 which allows the screw extender instrument 80 to be rigidly constrained to the screwdriver instrument 92. The drive interface 94 may include a plurality of flat faces or straight lobes configured to mate with the screwdriver body 92. The proximal end of the inner shaft 84 may include a ribbed neck 98 having a plurality of longitudinal ribs extending along the length of the inner shaft 84.

With emphasis on FIG. 9, the screwdriver instrument 92 may include a two-piece body. A first portion 102 may include a handle portion configured to receive the ribbed neck 98 of the inner shaft 84. A second portion 104 may include a tubular body configured to receive the outer shaft 82 of the screw extender instrument. A female drive seat 106 may mate with the drive interface 94 of the outer sleeve 82. A flexible mechanical spring 108 may engage with the groove 96 in the back portion of the screw extender 80. The screwdriver instrument 92 allows the user to apply the necessary torque to insert the screw into bone.

Figure 10A:
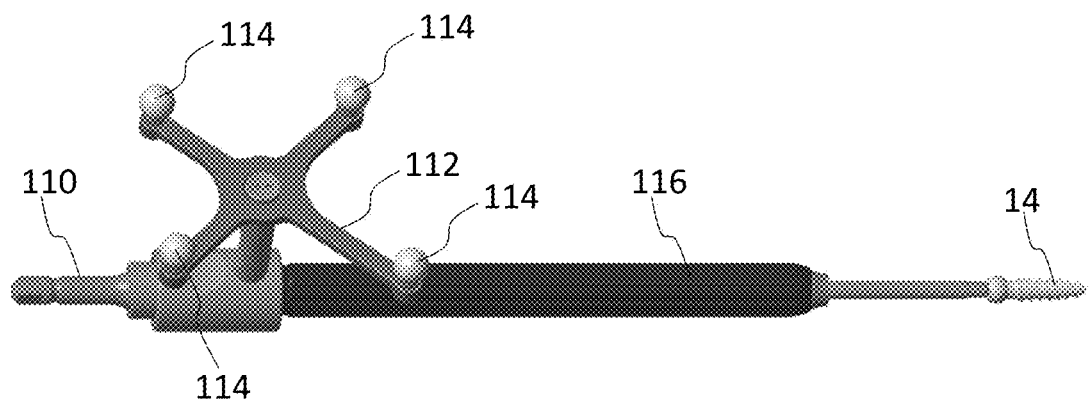
FIG. 10A shows a navigated robotic screwdriver with an array of tracking markers according to one embodiment.
Figure 10B:
FIG. 10B shows a navigated machine vision screwdriver according to one embodiment.
Figure 10C:
FIG. 10C shows a navigated robotic screwdriver with a two marker array according to one embodiment.

Turning now to FIGS. 10A-10C, the screwdriver 92 and/or screw extender instruments 40, 60, 70, 80 may be provided with additional elements for use with navigated and/or robotic techniques. In navigated and/or robot-assisted surgical procedures, one or more instruments may be tracked using a reference element, array, dynamic reference array, or other suitable tracking device or method. The tracking and/or robotic system may include one or tracking markers, which are attached or attachable to the instrument and allow for the system to detect and localize the position of the instrument in three-dimensional (3D) space. A computer platform in combination with a camera tracking system or other 3D localization system may be utilized to track in real-time: the position, rotational orientation, relative location, and movement of the instrument throughout the surgical procedure. Examples of surgical robotic and/or navigation systems can be found, for example, in U.S. Pat. Nos. 10,675,094 and 9,782,229, which are incorporated by reference herein in their entireties for all purposes.

In FIG. 10A, the navigated robotic screwdriver 110 includes a navigation feature, such as a tracking array 112, according to one embodiment. The tracking array 112 may secure a plurality of tracking markers 114, such as passive or active markers, in a given configuration. The tracking markers 114 may include optical spherical passive markers, for example. Alternatively, an array of discs may be used to navigate the screwdriver 110. The tracking array 112 may be axially constrained or attached to the screwdriver 110 and used to locate the axis and location of the tip of the screw 14 for navigated placement of screws 14. The instrument 110 may have an outer body portion 116 with an outer diameter sized and configured to mate with a guide tube of a robotic system. The body portion 116 of the driver 110 may be integral or may mate with an instrument with the desired outer diameter configured to match the end effector guide tube of the robot. When the body 116 of the screwdriver 110 is received through the guide tube of the robot, the robot further allows for guidance of the screw 14 along a pre-scribed trajectory.

In FIG. 10B, the navigation machine vision screwdriver 120 uses the geometry of the driver itself to navigate the screwdriver 120. A machine learning algorithm may be used to recognize the geometry and/or appearance of a known instrument and track the instrument 120 with visible light. One or more machine vision targets 122, 124 on the body of the screwdriver 120 may aid in instrument recognition and tracking by a navigation and/or robotic system. The machine vision targets 122, 124 may include longitudinal, circumferential, or other suitable targets that are marked, coated, or cut directly on the body of the screwdriver 120. For example, longitudinal targets 122 aid in tracking the orientation and rotation of the instrument, while circumferential targets 124 aid in tracking the distance to the tip of the instrument 120. Unique patterns, spacings, sizes, and shapes of these targets 122, 124 can allow the navigation and/or robotic system to differentiate between otherwise visually similar instruments. One or more areas of the instrument 120 may include non-reflective coatings and surface treatments 126 to reduce the effect of reflections or glare from bright operative lights. Similarly, machine vision targets 122, 124 may also be used to track the screw extenders 40, 60, 70, 80 after the screws 134 have been placed in the vertebral bodies.

In FIG. 10C, the navigated robotic screwdriver 130 includes a two marker array with fiducial markers 132 for navigated and/or robotic screw placement. For example, a pair of fiducial markers 132 may be attached to the screwdriver 130 or directly to the screw extenders 40, 60, 70, 80. The fiducial markers 132 may be passive spherical markers or discs, for example. An array of two or more markers 132 may be aligned with the central axis A of the instrument 130 and screw 14. Attaching an array with two or more markers 132 aligned with the central axis A of the screw 14 at a known distance from the tip 134 of the screw 14 allows tracking of the orientation of the central axis A of the screw 14 and the location of its tip 134, but not its rotation.

The navigated screwdrivers allow for accurate placement of the screw 14 to a pre-planned location along with recording of the final position of the screw 14 for use with subsequent vertebral body tracking. The varying methods for tracking instruments including the screw extenders allow for varying slimness and complexity of marker and navigated feature design, robustness of tracking, robustness of differentiation between simultaneously tracked instruments, computational resources required, and/or detection of loss of navigation integrity.

Figure 11:
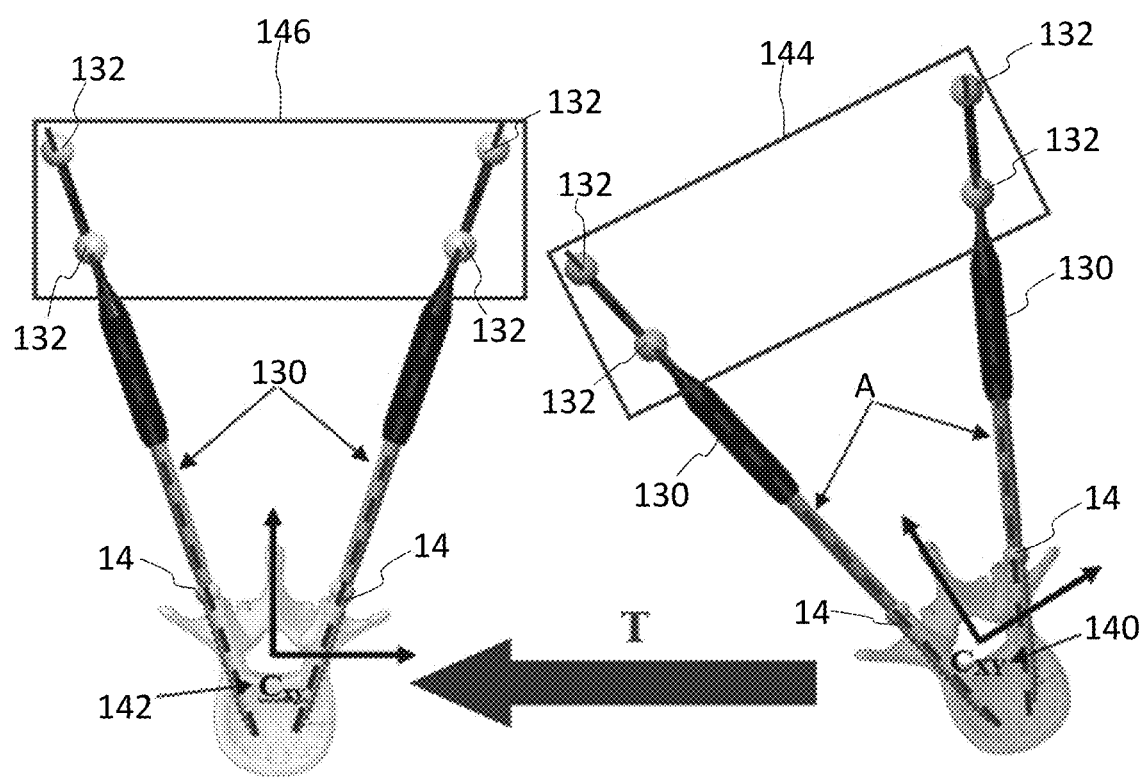
FIG. 11 shows an example of vertebral body tracking with screw extender instruments and four fiducial markers.

Turning now to FIG. 11, bone tracking with four fiducial markers 132 is shown. In FIG. 11, first and second pedicle screws 14 are inserted into bone at an initial position 140 in space. Once the screws 14 have been placed, the screw extender instruments 130 continue to track the location and orientation of the vertebral body, sacrum, and/or pelvis using the location and orientation of the placed screws 14. A transformation T of the location and/or orientation of the bone in space due to translation and/or rotation results in a subsequent position 142 identified by the system. The instruments 130 thereby allow for continued tracking of the bone. Although FIG. 11 is described with respect to tracking instrument 130, it will be appreciated that the tracking methods may apply to any of the screw extender instruments or other navigatable instruments described herein.

According to one embodiment, a system and method for individual extender array tracking may include one or more of the following steps.

(1) The orientation of the central axes A of the screws 14 are recorded at the completion of navigated insertion of screws 14 into the vertebral body at initial position 140.

(2) Screw extenders 130 are recorded by the motion tracking system during manipulation of the spine.

(3) The vectors defining the central axes A of the screw extenders 130 are calculated. For discs or markers 132 placed along the central axis A, this is the difference in coordinates between the discs or markers 132. If, at any time, the relative orientation of these vectors becomes significantly different than the vectors of the placed screws 14, navigation integrity has been lost and the system will stop tracking.

(4) These two vectors are compared against the original orientation of the central axes A of the screws 14 to define the transformation matrix that corresponds to the rigid body translation and rotation of the vertebral body.

(5) The transformation matrix is applied to the vertebral body coordinate system 140 to update its translation and rotation in space to position 142.

According to another embodiment, a system and method for combined extender array tracking may include one or more of the following steps.

(1) The orientation and position of the central axes A of the screws 14 are recorded at the completion of navigated insertion of screws 14 into the vertebral body.

(2) Locations of the fiducial markers 132 and/or instrument 130 are modeled by calculating their distance along the central axes A of the screw extenders 130.

(3) These locations define a unique array 144 or combined instrument model to be tracked and recognized by the vision system. If the screw extenders 130 move significantly with respect to each other, a different array 146 or combined instrument model cannot be recognized and the system will stop tracking.

(4) These arrays 144, 146 or combined instrument models are recorded by the motion tracking system during manipulation of the spine.

(5) The coordinate system of the arrays 144, 146 or combined instrument models are compared against their modeled original coordinate systems 140 to define a transformation matrix that corresponds to the rigid body translation and rotation of the vertebral body.

(6) The transformation matrix is applied to the vertebral body coordinate system to update its translation and rotation in space to position 142.

The transformation matrix is shown below in equation (1):

$$x_j = T_{ij}X_i \rightarrow \begin{bmatrix} x \\ y \\ z \\ 1 \end{bmatrix} = \begin{bmatrix} r_{xx} & r_{xy} & r_{xz} & t_x \\ r_{yx} & r_{yy} & r_{yz} & t_y \\ r_{zx} & r_{zy} & r_{zz} & t_z \\ 0 & 0 & 0 & 1 \end{bmatrix} \begin{bmatrix} X \\ Y \\ Z \\ 1 \end{bmatrix}$$

With 26 individual vertebrae, the sacrum, and pelvis, many arrays and objects may need to be simultaneously recognized and tracked. Multiple methods may be used to allow recognition of the screw extenders and vertebral body they are tracking:

(1) Position Cross-Reference: The position of the tip of the screw extender is calculated and ordered according to its height along patient's central axis. Vertebral bodies may be ordered superior to inferior and do not exchange locations during surgical intervention. Positions closer to the right of the patient coordinate system or the right of the vertebral body coordinate system can be identified as the right pedicle screw, or left pedicle screw conversely.

(2) Unique Fiducial Array: A unique array of fiducial markers or discs could be recognized by their unique distances between markers.

(3) Unique Machine Vision Targets: A unique pattern, size, or color of machine vision targets may be used to differentiate each screw extender.

(4) Unique Combined Extender Array: Utilizing the method for combined extender array tracking above, the unique trajectory and position of the screws creates a unique array pattern which can be recognized by their unique distances between markers.

Once vertebral bodies are tracked, changes in position and orientation can be used to provide feedback to the user, such as displaying the current position and orientation of vertebral bodies, calculating spinal alignment parameters such as lordosis and kyphosis, and/or calculating foraminal height and estimated tension/compression placed on neural elements from the displacements of tracked adjacent vertebral bodies.

Tracking of vertebral bodies allows for real time intraoperative feedback to be provided to the user on measures that typically require discrete x-ray images to be taken. Spinal alignment, neural decompression, and other clinically relevant parameters can be assessed continuously for the user to adapt their intraoperative intervention to achieve desired surgical goals. Anatomy can be visualized more accurately by displaying the locations of bony anatomy in their current locations instead of relying on a radiograph that does not reflect surgical changes.

Figures 12A, 12B, 12C:
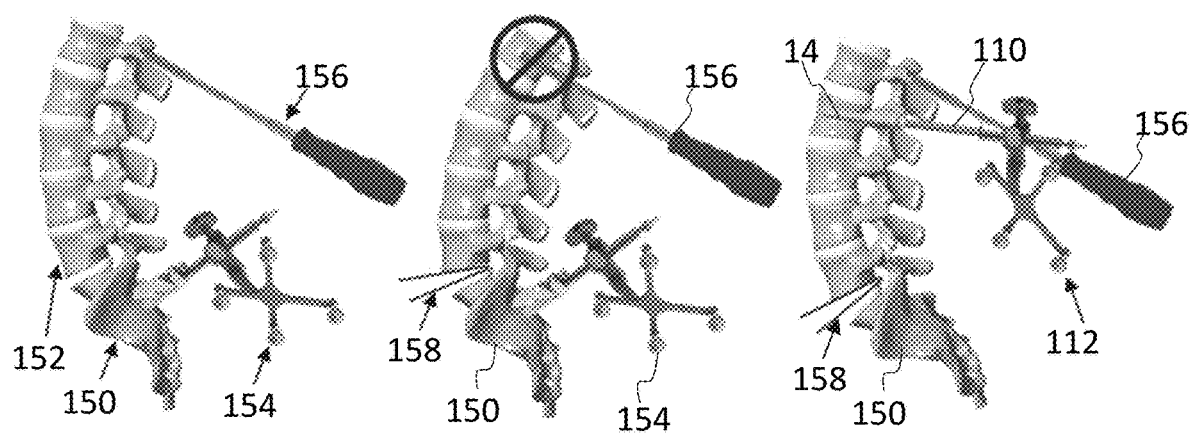
FIGS. 12A-12C show a system of minimizing navigation integrity errors by replacing a traditional dynamic reference base with a local dynamic reference base using a navigated screw extender instrument.
Figure 13A:
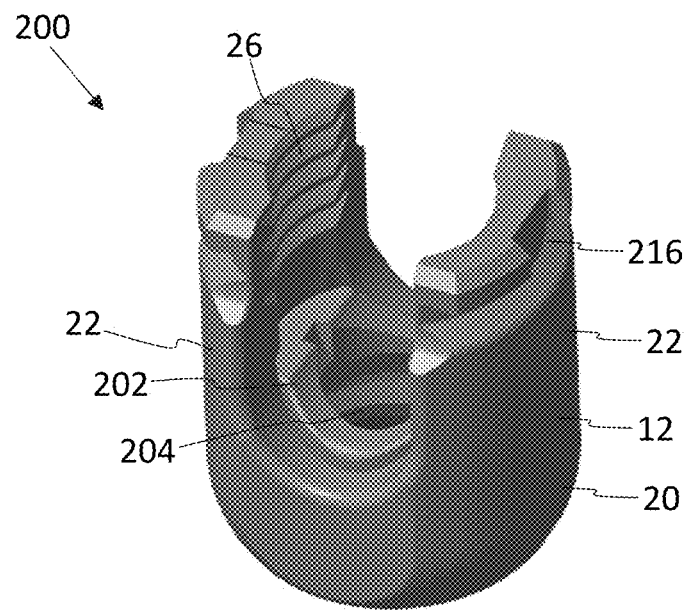
FIGS. 13A-13B show a perspective view and a cross-sectional view, respectively, of a modular tulip head assembly with an inner conical taper for the clip according to one embodiment.
Figure 13B:
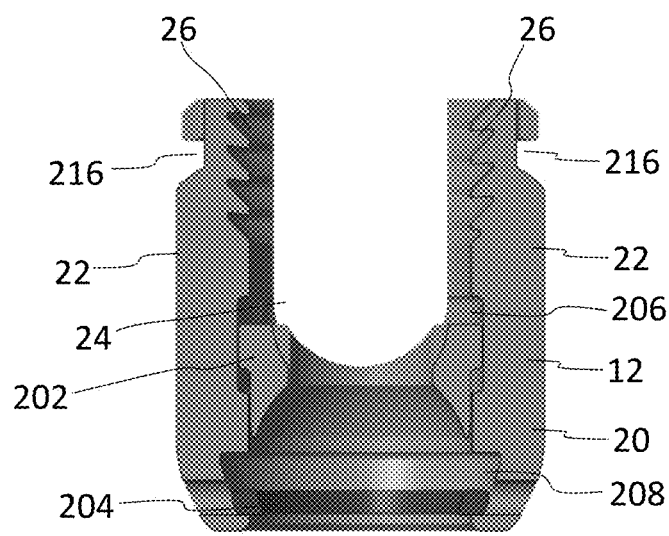
Figure 14:
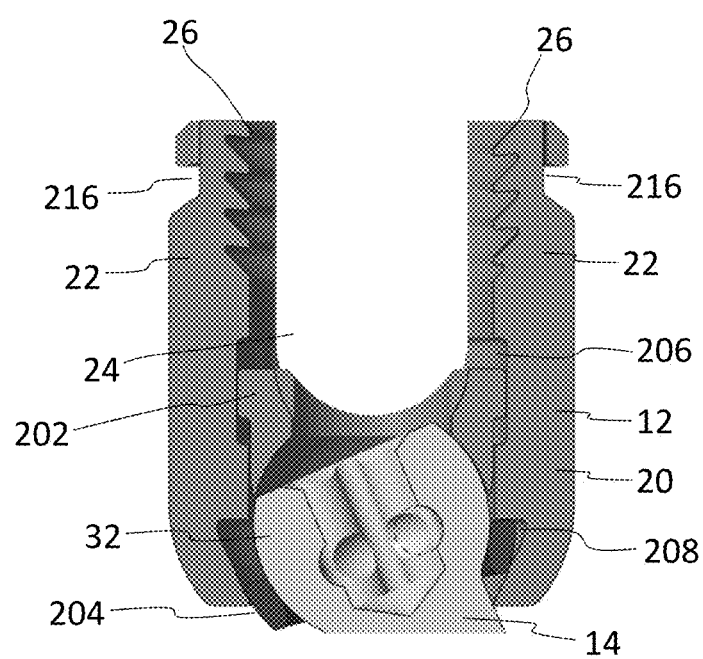
FIG. 14 is a cross-sectional view of a modular tulip head inserted onto the screw head with a spherical taper for the clip according to one embodiment.
Figure 15:
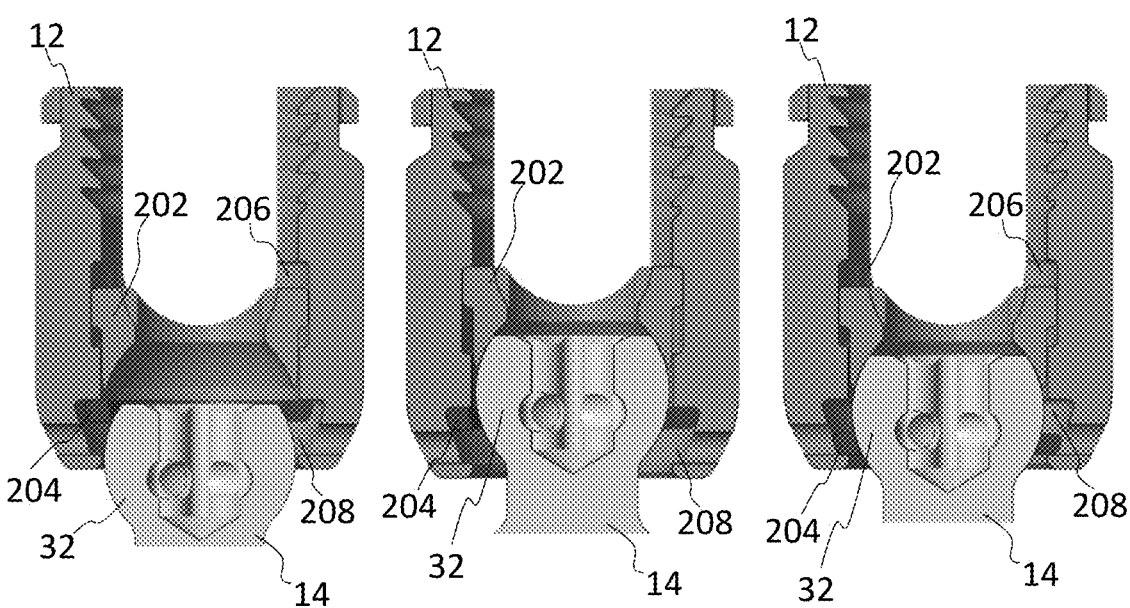
FIGS. 15A-15C depict a method of inserting the modular tulip head with the clip onto the screw head according to one embodiment.

Turning now to FIGS. 12A-12C, navigation integrity may be improved by using a placed screw 14 and screw extender 110 as a local Dynamic Reference Base (DRB) instead of a traditional DRB anchored further from the vertebral body being manipulated. The DRB is used to locate imaging to patient anatomy, and if patient anatomy displaces outside of rigid body motion, then navigation integrity is affected. When the DRB is instead attached closer to an area of interest, the navigation integrity error can be reduced.

FIGS. 12A-12B show traditional placement of the DRB 154 on the spine. For example, a traditional DRB 154 may be placed on the sacrum 150 below the lumbar spine 152. The navigated tool 156 may be placed on the posterior elements of L1 or other vertebrae. As shown in FIG. 12B, when lordosis 158 is added between L5 and S1, the sacrum 150 stays at the same place with respect to the DRB 154, but the location of tool 156 changes and is now located in the middle of the vertebral body. The navigation system would erroneously show the tool position on the posterior elements, thereby resulting in an inaccuracy in navigation.

In FIG. 12C, the traditional DRB 154 is replaced with the implanted screw 14 and screw extender instrument 110. Although instrument 110 is shown, it will be appreciated that any of the navigatable screw extender instruments may be substituted. The array 112 of the screw extender 110 acts as the local DRB to locate imaging. The screw 14 and screw extender tool 110 and resulting tracking are now located in close proximity to the instrument 156. In this configuration, a change in the lordosis 158 does not result in a change of the apparent tool location. Thus, the navigation system properly shows the position of tool 156 on the posterior elements, thereby resulting in accurate navigation. In other words, use of the screw extenders 110 as a local DRB allows for positioning of DRBs in additional bony anatomy closer to areas of interest to reduce errors in navigation integrity caused by non-rigid motion of the spine. This allows navigation integrity to be maintained more readily in longer constructs across many flexible portions of the spine or in interventions where the spine is flexible, for example, in pediatric deformity or when significant osteotomies are performed.

Turning now to FIGS. 13-16, examples of the modular tulip head assembly 200 are shown. After the screw 14 is inserted into bone, with or without navigation and/or robotic assistance, the modular tulip head 12 is inserted onto the screw head 32, thereby forming a polyaxial assembly. The modular head design allows for insertion of the modular tulip head 12 onto the screw head 32 with or without the screw extender 40, 60, 70, 80. An inserter instrument 210 may include a sensing mechanism to ensure correct deployment of the modular head 12 on the screw 14. The simple and robust component design simplifies manufacturing while reducing tolerance stack to improve reliability and strength.

As described above for FIGS. 1 and 2, the modular tulip head 12 includes a body 20 with two arms 22 defining a channel for receiving the spinal rod 18. The tulip assembly 200 further includes a saddle 202 and a clip 204. The saddle 202 includes an upper surface for receiving the rod 18 and a bottom surface for receiving the top of the screw head 32. The clip 204 may include a loop, ring, split-ring, snap ring, or other suitable retaining ring. The inner bore 24 defines a first groove 206 above a second groove 208. The saddle 202 is housed within the first groove 206 and the clip 204 is housed within the second groove 208 with excess clearance to allow them each to travel along the central axis of the tulip 12. The groove 208 that the clip 204 is housed within tapers such that the bottom of the groove 208 has minimal clearance over the ring 204 while the top of the groove 208 has additional clearance. In the embodiment shown in FIGS. 13A-13B, the outer surface of the clip 204 and the groove 208 in the inner surface of the tulip 12 is conically tapered. In the embodiment shown in FIG. 14, the outer surface of the clip 204 is spherically tapered, and the recess 208 in the inner surface of the tulip 12 has two radiused tapers so that the clip 204 can angle or tilt with the screw 14.

With emphasis on FIGS. 15A-15B, a method of assembling the tulip head 12 onto the screw head 32 of screw 14 is shown. In FIG. 15A, when the spherical head 32 of the modular screw 14 is inserted into the lower bore 24 of the tulip 12, the head 32 contacts the bottom of the clip 204 and moves the clip 204 upward to the upper portion of the clip groove 208. In FIG. 15B, further insertion of the spherical head 32, upward into the tulip head 12, expands the clip 204. The additional clearance of the groove 208 allows the clip 204 to expand until the center of the spherical head 32 of the screw 14 has passed through the clip 204. The excess clearance in the saddle groove 206 provides sufficient clearance to allow the travel of the spherical head 32 of the screw 14. In FIG. 15C, once the clip 204 passes the center of the spherical head 32 of the screw 14, the modular head 12 has been assembled to the screw 14. Forces directed to dissociate the screw 14 from the modular head 12 translate the clip 204 down against the smaller portion of the groove 208 in the modular head 12 which prevents the clip 204 from expanding, thereby preventing the screw 14 from disassembling from the modular head 12.

Figure 16:
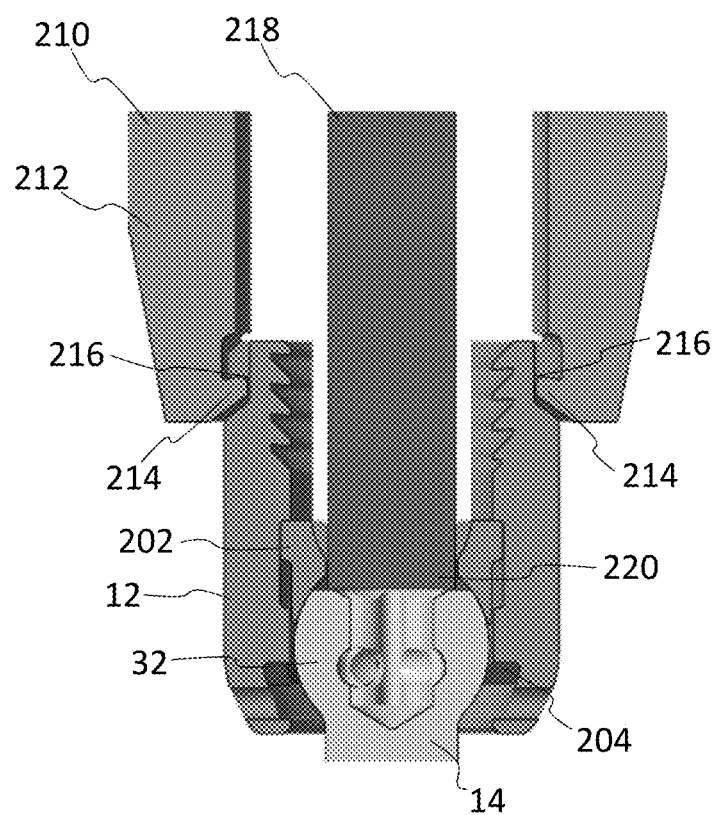
FIG. 16 shows a cross-sectional view of a head inserter instrument holding the modular tulip head according to one embodiment.

Turning now to FIG. 16, a head inserter instrument 210 is shown engaged with the tulip head 12. The head inserter instrument 210 holds the tulip head 14 with an external sleeve 212. The external sleeve 212 may include one or more inwardly facing prongs 214 configured to engage with one or more recesses or grooves 216 on the outer diameter of the tulip head 12. The head inserter instrument 210 may include a sensing pin 218 that extends beyond the end of the sleeve 212. A distal tip 220 of the sensing pin 218 is configured to contact the top of the head 32 of the screw 14. When the sensing pin 218 is depressed by the modular screw head 32, the external sleeve 212 is permitted to be actuated, allowing the user to release the external sleeve 212 from the tulip head 12. This creates a mechanism that ensures that the spherical head 32 of the screw 14 is sufficiently inserted into the modular head 12. Alternatively, if the screw extender instrument 40, 60, 70, 80 is still connected to the screw head 32, the sensing pin 218 may contact the top of the screw extender 40, 60, 70, 80 to allow the modular tulip head 12 to be inserted over the screw extender 40, 60, 70, 80 and assembled to the screw 14.

Navigation features may be attached to the inserter 210 to allow for insertion when the screw 14 cannot be visualized, such as when tissue obscures the screw head 32 in minimally invasive approaches. One or more navigation arrays may be attached to the outer sleeve 212 of the inserter 210 to allow for navigated insertion of the tulip head 12 onto the known location of the screw head 14. A stray marker attached to and moved by the sensing pin 218 allows the navigation system to recognize when the tulip head 12 becomes fully inserted and provides feedback to the user during the assembly. The navigated stray marker also provides a secondary feedback to the system and user to confirm deployment.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all components of the various devices disclosed above may be combined or modified in any suitable configuration.

What is claimed is:

1. A system for installing a modular orthopedic fixation assembly comprising:
    a modular screw including a screw head defining a drive and engagement recess and a shaft configured for engaging bone;
    a screw extender instrument configured to engage with the screw head, wherein the screw extender instrument includes an outer sleeve and an inner shaft extending through the outer sleeve receivable in the drive and engagement recess of the screw head, wherein movement of the outer sleeve or inner shaft secures the screw extender instrument to the screw head;
    a modular tulip head assembly including a tulip head having two arms defining a rod slot therebetween and a saddle and a clip configured to secure the screw head of the modular screw in the tulip head; and
    a threaded locking cap threadable between the two arms of the tulip head to secure a rod therein,
    a head inserter instrument having an external sleeve with inwardly facing prongs configured to engage with a groove on an outside of the tulip head, and a sensing pin configured to contact the screw head, thereby allowing for release of the external sleeve when the tulip head is fully seated on the screw head,
    wherein the screw extender instrument includes one or more ball bearings receivable in the drive and engagement recess of the screw head, thereby allowing for a rigid connection between the screw extender instrument and the screw head,
    wherein the ball bearings are caged within an assembly at the outermost and innermost extensions of their travel by ramped spherical cuts.

2. The system of claim 1, wherein the drive and engagement recess in the screw head includes a recessed drive portion configured to interface with the outer sleeve and one or more recessed engagement portions configured to interface with the one or more ball bearings of the screw extender instrument.

3. The system of claim 2, wherein the engagement portions each define an undercut with a circular cross-section sized and dimensioned to interface with the ball bearing of complimentary size and shape.

4. The system of claim 2, wherein the ramped spherical cuts define a helical ramp at a distal end of the inner shaft, wherein when the inner shaft is rotated and/or translated, the ball bearing is seated into the engagement portion of the screw head.

5. The system of claim 2, wherein the screw extender instrument includes a pair of ball bearings and the inner shaft includes a pointed tip that when translated downwardly forces the ball bearings outwardly into the engagement portions of the screw head.

6. The system of claim 1, wherein the screw extender instrument couples to a screw driver instrument to allow a user to align the screw with an intended trajectory and apply torque to the screw.

7. The system of claim 1, wherein the screw extender instrument includes a tracking element configured to be tracked by a navigation or robotic system.

8. The system of claim 7, wherein the tracking element includes a two marker array with fiducial markers aligned along a central axis of the screw for navigated and/or robotic screw placement.

* * * * *